United States Patent
Wei et al.

(10) Patent No.: US 12,295,695 B2
(45) Date of Patent: May 13, 2025

(54) METHOD OF MANAGING MONITORING DATA, PROBE ASSEMBLY, MANAGEMENT SYSTEM OF MONITORING DATA

(71) Applicant: EDAN INSTRUMENTS, INC., Shenzhen (CN)

(72) Inventors: Wenyu Wei, Shenzhen (CN); Meisheng Li, Shenzhen (CN); Dewei Chen, Shenzhen (CN); Chong Luo, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 65 days.

(21) Appl. No.: 18/170,564

(22) Filed: Feb. 17, 2023

(65) Prior Publication Data
US 2023/0190099 A1    Jun. 22, 2023

Related U.S. Application Data

(63) Continuation of application No. PCT/CN2020/110033, filed on Aug. 19, 2020.

(51) Int. Cl.
*A61B 5/00* (2006.01)
*A61B 5/1455* (2006.01)
(Continued)

(52) U.S. Cl.
CPC ............ *A61B 5/0011* (2013.01); *A61B 5/002* (2013.01); *A61B 5/14552* (2013.01);
(Continued)

(58) Field of Classification Search
CPC ........ H04L 67/12; G16H 40/20; G16H 40/67; G16H 50/20; G16H 50/70; A61B 5/0011;
(Continued)

(56) References Cited

U.S. PATENT DOCUMENTS

2014/0163409 A1    6/2014   Arndt
2016/0051172 A1*   2/2016   Lin ................... A61B 5/14552
                                                      600/407
(Continued)

FOREIGN PATENT DOCUMENTS

CN    102688070 A    9/2012
CN    111107509 A    5/2020
EP      1315446 B1   4/2008

OTHER PUBLICATIONS

International search report and Written Opinion of the International Search Authority, International Application No. PCT/CN2020/110033, mailed May 21, 2021(15 pages).
(Continued)

*Primary Examiner* — Dionne Pendleton

(57) ABSTRACT

The present application relates to the technical field of medical monitoring. Specifically disclosed are a method for managing monitoring data, a probe assembly, and a system for managing monitoring data. The method for managing monitoring data based on the probe assembly comprises the following steps: establishing a communication connection with a first monitor; in response to a data roll-out instruction, receiving first monitoring data from the first monitor, and after the transmission of the first monitoring data is completed, breaking the communication connection with the first monitor; establishing a communication connection with a second monitor; and sending at least the first monitoring data to the second monitor, and cooperating with the second monitor to execute a monitoring task.

19 Claims, 11 Drawing Sheets

(51) Int. Cl.
*G16H 40/67* (2018.01)
*H04L 67/12* (2022.01)

(52) U.S. Cl.
CPC .............. *G16H 40/67* (2018.01); *H04L 67/12* (2013.01); *A61B 2562/00* (2013.01)

(58) Field of Classification Search
CPC ... A61B 5/002; A61B 5/14552; A61B 5/6814; A61B 2560/0475; A61B 2562/0215; A61B 2562/04; A61B 2562/085; A61B 5/0205; A61B 5/02055; A61B 5/053; A61B 5/11; A61B 5/14551; A61B 5/14553; A61B 5/1495; A61B 5/16; A61B 5/164; A61B 5/378; A61B 5/389; A61B 5/398; A61B 5/6889; A61B 5/7232; A61B 5/7264; A61B 5/7267; A61B 5/7278; A61B 5/74; A61B 5/742; A61B 5/7475; A61B 5/0077; A61B 5/065; A61B 8/4263; A61B 8/4416; A61B 8/4427; A61B 8/4438; A61B 8/4455; A61B 8/4472; A61B 8/4483; A61B 8/461; A61B 8/463; A61B 8/467; A61B 8/54; G01D 18/00; Y10S 323/911; G01K 1/026; G01K 1/08; G01K 1/14; G01K 1/20; G01K 13/02; G01K 2215/00; G01K 7/00; G01S 15/899; G01S 7/52084; G12B 15/06

See application file for complete search history.

(56) References Cited

U.S. PATENT DOCUMENTS

2018/0042560 A1    2/2018  Mannheime et al.
2020/0275908 A1*   9/2020  Oura ..................... G01S 15/899

OTHER PUBLICATIONS

European Search Report, European Application No. 20949803.9, mailed Nov. 29, 2023 (9 pages).

* cited by examiner

METHOD OF MANAGING MONITORING DATA, PROBE ASSEMBLY, MANAGEMENT SYSTEM OF MONITORING DATA

CROSS REFERENCE TO RELATED APPLICATIONS

This application is a continuation-application of the International Patent Application No. PCT/CN2020/110033, filed on Aug. 19, 2020, which is hereby incorporated by reference in its entirety.

TECHNICAL FIELD

The present disclosure relates to the field of medical monitoring, and in particular to a method of managing monitoring data, a probe assembly, and a management system of the monitoring data.

BACKGROUND

As monitors are widely used in the medical field currently, patients are increasingly dependent on medical monitors to monitor their vital characteristics. However, usage of medical monitoring devices that are commercially available in the market may be limited by locations where the devices are placed. When a patient moves from one location to another, the medical monitoring device needs to be changed, and a monitoring probe needs to be re-worn, such that monitoring may be interrupted. Further, the changing may be complicated, and a working efficiency of a doctor may be reduced.

SUMMARY OF THE DISCLOSURE

To solve the above technical problem, the present disclosure provides a method of managing monitoring data, a probe assembly, and a management system of the monitoring data. According to the present disclosure, bed-transfer operations may be simplified, and the monitoring may be continuous. The doctor may view monitoring data before the bed-transfer operations, such that the doctor may work efficiently.

In a first aspect, a method of managing monitoring data based on a probe assembly is provided and includes: establishing, by the probe assembly, communication connection with a first monitor; receiving, by the probe assembly in response to a data-transfer instruction, first monitoring data from the first monitor; after transferring the first monitoring data being completed, disconnecting the communication connection with the first monitor; establishing, by the probe assembly, communication connection with a second monitor; and sending, by the probe assembly, at least the first monitoring data to the second monitor and performing, by the probe assembly, a monitoring task cooperatively with the second monitor.

In a second aspect, a probe assembly is provided and includes a plurality of probes. The plurality of probes in the probe assembly are configured to cooperate with each other to perform the operations of: establishing communication connection with a first monitor; receiving, in response to a data-transfer instruction, first monitoring data from the first monitor; after transferring the first monitoring data being completed, disconnecting the communication connection with the first monitor; establishing communication connection with a second monitor; and sending at least the first monitoring data to the second monitor and performing a monitoring task cooperatively with the second monitor.

In a third aspect, a management system of monitoring data is provided and includes: a probe assembly, a first monitor, and a second monitor. The probe assembly is configured to operate cooperatively with the first monitor and the second monitor to perform the operations of: establishing communication connection with a first monitor; receiving, in response to a data-transfer instruction, first monitoring data from the first monitor; after transferring the first monitoring data being completed, disconnecting the communication connection with the first monitor; establishing communication connection with a second monitor; and sending at least the first monitoring data to the second monitor and performing a monitoring task cooperatively with the second monitor.

BRIEF DESCRIPTION OF THE DRAWINGS

In order to illustrate the technical solutions in the embodiments of the present disclosure more clearly, the accompanying drawings used in the description of the embodiments are briefly described in the following. Obviously, the following drawings show only some of the embodiments of the present disclosure. Other drawings may be obtained based on the following drawings without any creative work by any ordinary skilled person in the art.

DETAILED DESCRIPTION

The technical solutions in the embodiments of the present disclosure will be clearly and completely described below by referring to the accompanying drawings in the embodiments of the present disclosure. Obviously, the embodiments described herein show only a part of but not all of the embodiments of the present disclosure. All other embodiments obtained without creative work by any ordinary skilled person in the art based on the embodiments in the present disclosure shall fall within the scope of the present disclosure.

To be noted that the patient in the embodiments of the present disclosure may be a pregnant lady, an obstetrical and gynaecological patient, an in-bed patient or any other patient whose physical data needs to be monitored. In the following, the technical solution in the embodiments of the present disclosure may be illustrated clearly and completely by taking the pregnant lady as an example.

Figure 1:
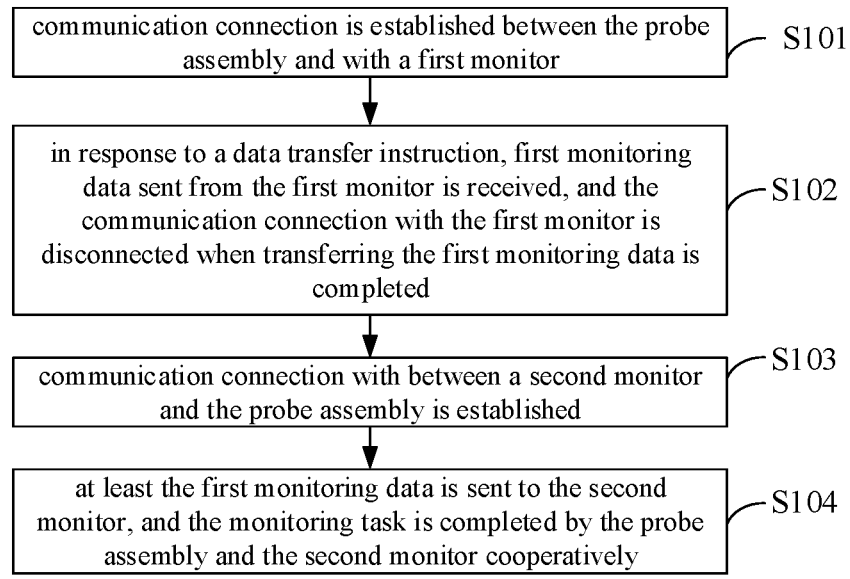
FIG. 1 is a flow chart of a method of managing monitoring data based on a probe assembly according to a first embodiment of the present disclosure.

As shown in FIG. 1, the method includes the following operations.

In an operation S101, a communication connection is established between the probe assembly and a first monitor.

Specifically, the probe assembly includes at least one probe. The communication connection is established between the at least one probe and the first monitor. The communication connection includes at least one of a Bluetooth communication connection, an infrared communication connection, an radio frequency ID ultra-wideband (UWB) communication connection, a ZigBee communication connection, a WI-FI communication connection, and so on.

In an operation S102, in response to a data transfer instruction, first monitoring data sent from the first monitor is received, and the communication connection with the first monitor is disconnected when transferring the first monitoring data is completed.

Specifically, when the pregnant lady needs to be transferred from a waiting room to a delivery room, the probe assembly is disconnect from the first monitor in the waiting room and establishes a communication connection with a second monitor in the delivery room.

In this situation, a medical staff may click a "transfer out" button on the first monitor, and the first monitor sends the data transfer instruction to all probe assemblies connected to the first monitor. At the same time, the first monitor packages the current to-be-transferred first monitoring data of the pregnant lady based on an agreed transferring protocol, and caches the packaged first monitoring data into a memory.

The first monitoring data includes at least: monitoring data collected by the probe assembly, emergency treatment information recorded by the first monitor, and information of the pregnant lady. The monitoring data collected by the probe assembly may include: a monitoring time length, a monitoring starting time point, a monitoring end time point, a bed-transfer starting time point, a bed-transfer end time point, a fetal heartbeat signal of an uncertain time length, a fetal movement signal, a uterus contraction pressure signal, and a heart rate signal. Further, the first monitoring data may include parameters of the first monitor and third access information of the first monitor.

A probe that serves as a temporary host probe has an internal memory block to cache the first monitoring data from the first monitor. Based on the TCP/IP protocol, the probe that serves as the temporary host probe may determine whether transmitting the first monitoring data is completed based on a return value of a receiving data interface.

When a temporary monitoring system is disconnected from the first monitor, the temporary monitoring system is not communicating with any monitor. At this time point, the temporary monitoring system is in a transferring-out period. Since the pregnant lady is wearing the probe assembly at all times, a monitoring task is not interrupted, and the temporary monitoring system is still collecting relevant monitoring data. Further, other probes may send respectively collected monitoring data to the probe that serves as the temporary host probe. The probe that serves as the temporary host probe can have a plurality of internal memory blocks for caching the monitoring data collected by each of the other probes during the transferring-out period and/or the monitoring data collected by the probe that serves as the temporary host probe itself.

In an operation S103, a communication connection between a second monitor and the probe assembly is established.

To be noted that when the probe assembly includes only one probe, i.e., when there is only one probe in the temporary monitoring system, the temporary monitoring system does not need to be decomposed, and the communication connection between the only one probe and the second monitor is established directly.

When the probe assembly includes at least two probes, the temporary monitoring system needs to be decomposed firstly to obtain at least two probes that are not connected to each other, and then the communication connection between each probe and the second monitor is established in order to reconstruct a monitoring system consisting of the second monitor and the probe assembly.

In an operation S104, at least the first monitoring data is sent to the second monitor, and the monitoring task is completed by the probe assembly and the second monitor cooperatively.

Specifically, when the probe that serves as the temporary host probe in the operation S102 successfully establishes the communication connection with the second monitor, a transferring-in period is entered. Monitoring data collected by the other probes is no longer sent to the probe that serves as the temporary host probe in the operation S102. At the same time, the probe that serves as the temporary host probe in the operation S102 sends the first monitoring data from the first monitor, the monitoring data collected by each of the other probes during the transferring-out period, and the monitoring data collected by the probe that serves as the temporary host probe itself, to the second monitor.

According to the present disclosure, a method of managing monitoring data based on the probe assembly is provided. While the patient is being transferred from one bed to another, the probe assembly independently performs the monitoring task in response to the data-transfer instruction and stores the monitoring data from the original monitor. In this way, after the probe assembly establishes the communication connection with another monitor, the probe assembly may transfer the first monitoring data that is collected by the original monitor and before the patient is being transferred to the another monitor. Therefore, the monitoring may be performed continuously, and the doctor may view the first monitoring data that is collected before the patient is being transferred on the another monitor, and the working efficiency of the doctor may be improved. Furthermore, the pregnant lady is wearing the probe assembly while she is being transferred from one bed to another, the probe assembly may not be re-worn, such that the process of transferring the patient from one bed to another may be simplified.

The data-transfer instruction includes: first access information. The first access information may include access information for a particular probe. For example, the first access information may be an SSID and an access password of the temporary host probe.

Figure 2:
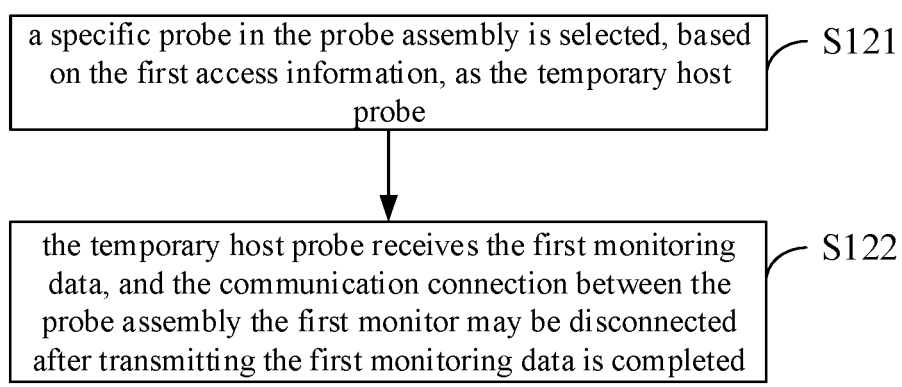
FIG. 2 is a flow chart of an operation S102 of the method shown in FIG. 1.

As shown in FIG. 2, the operation S102 includes the following.

In an operation S121, a specific probe in the probe assembly is selected, based on the first access information, as the temporary host probe.

Two methods of selecting the specific probe from the probe assembly to serves as the temporary host probe are listed below.

For a method 1, the probe assembly, in response to the data-transfer instruction, directly configure a pre-defined probe as the temporary host probe based on pre-defined rules. For example, in an actual obstetric fetal monitoring scenario, a fetal heart rate must be measured while monitoring a fetus. The probe assembly in the present embodiment may include three fetal heart probes, a US1, a US2, and a US3, and a uterine contraction pressure probe TOCO. The pre-defined probe may be the fetal heart probe US1. That is, the fetal heart probe US1 is configured as the temporary host probe of the temporary monitoring system.

For a method 2, the probe assembly, in response to the data-transfer instruction, selects a specific probe from a plurality of probes. The specific probe includes a probe that is currently in a first operation state. A power level and/or a signal strength of the probe that is currently in the first operation state is greater than a power and/or a signal strength of any other probe of the plurality of probes.

The method 1 in the above may be performed simply, and an operating principle of the method 1 may be easily understood. The probe, which is selected to serve as the temporary host probe for the temporary monitoring system each time while the patient is being transferred from one bed to another, may be fixed. The method 2 may be performed more flexibly. The signal strength may be maximized, ensuring smooth communication and enabling monitoring data to be transmitted. The remaining power of the probe may meet requirements of transferring from one bed to another, ensuring that the system is not shut down while the patient is being transferred from one bed to another, and leaving enough time for transferring the patient from one bed to another.

In an operation S122, the temporary host probe receives the first monitoring data, and the communication connection between the probe assembly the first monitor may be disconnected after transmitting the first monitoring data is completed.

Further, the probe that serves as the temporary host probe may, in response to the data-transfer instruction, send a responding instruction to the first monitor. At this time point, after the first monitor receives the responding instruction from the temporary host probe, the first monitor starts to send the first monitoring data to the probe that serves as the temporary host probe.

The temporary host probe receives the first monitoring data. A data packet between the first monitor and the temporary host probe is transferred based on the TCP/IP transfer protocol. When network communication is operating normally, the first monitoring data may be delivered correctly to the temporary host probe. When the network is operating abnormally, the data may be retransmitted for a plurality of times. When the network cannot be restored during retransmission, the user may be informed that the network is operating abnormally.

When the temporary host probe determines that the first monitor has completed data transmission, the temporary host probe may send a responding instruction to the first monitor indicating "the monitoring data is received successfully". After the first monitor receives the responding instruction indicating "the monitoring data is received successfully", the communication connection between the probe assembly the first monitor may be disconnected. At this time point, the temporary monitoring system is being in the transferring-out period.

Figure 3:
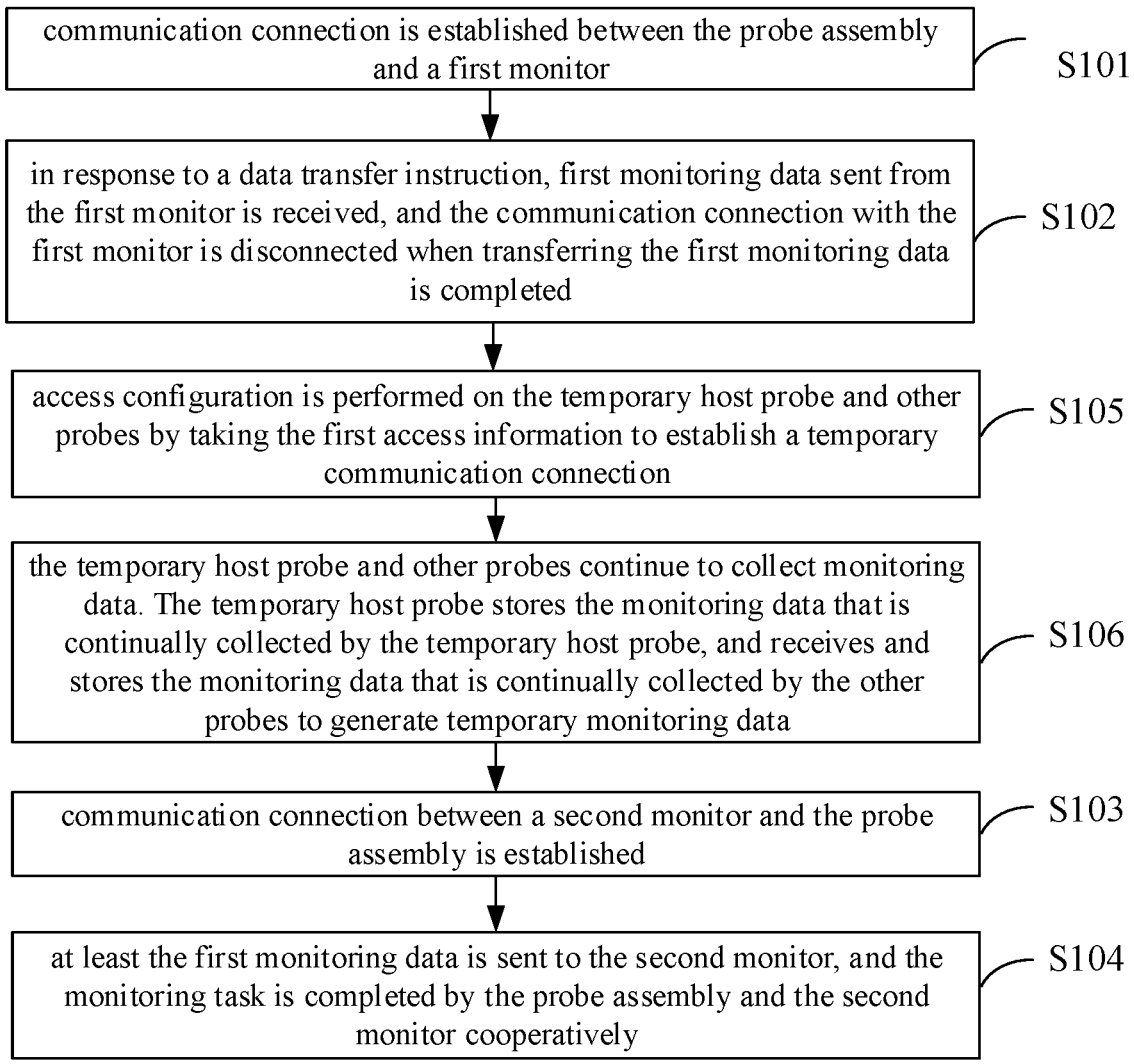
FIG. 3 is a flow chart of a method of managing monitoring data based on a probe assembly according to a second embodiment of the present disclosure.

As shown in FIG. 3, in some embodiments, before the operation S103, the method further includes the following operations.

In an operation S105, access configuration is performed on the temporary host probe and other probes by taking the first access information to establish a temporary communication connection.

Specifically, when the probe assembly includes only one probe, the temporary monitoring system has only one probe, and the only one probe serves as the temporary host probe. The temporary host probe may, in response to the data-transfer instruction, send the responding instruction to the first monitor. At this time point, after the first monitor receives the responding instruction from the temporary host probe, the first monitor starts to send the first monitoring data to the temporary host probe.

When the probe assembly includes at least two probes, the specific probe in the probe assembly may be selected as the temporary host probe based on the operation S121. All other probes are communicatively connected to the temporary host probe, and a temporary communication connection is established to form the temporary monitoring system. To be noted that only one probe is required to serve as the temporary host probe, and technically, any one probe may serve as the temporary host probe.

In an operation S106, the temporary host probe and other probes continue to collect monitoring data. The temporary host probe stores the monitoring data that is continually collected by the temporary host probe, and receives and stores the monitoring data that is continually collected by the other probes to generate temporary monitoring data.

The temporary host probe and the other probes cooperatively form the temporary monitoring system. At this time point, the temporary host probe and the other probes are in the transferring-out period and are no longer connected to any monitor. Since the probe assembly is worn by the pregnant lady during the transferring-out period, the monitoring task is not interrupted, and the temporary host probe and other probes continually collect the monitoring data.

Further, the temporary host probe stores the monitoring data that is continually collected by the temporary host probe and receives the monitoring data that is continually collected by the other probes. The temporary host probe has a plurality of internal memory blocks. The temporary host probe may receive the monitoring data that is continually collected by the other probes, and store the received monitoring data in the internal memory blocks to generate the temporary monitoring data.

Figure 4:
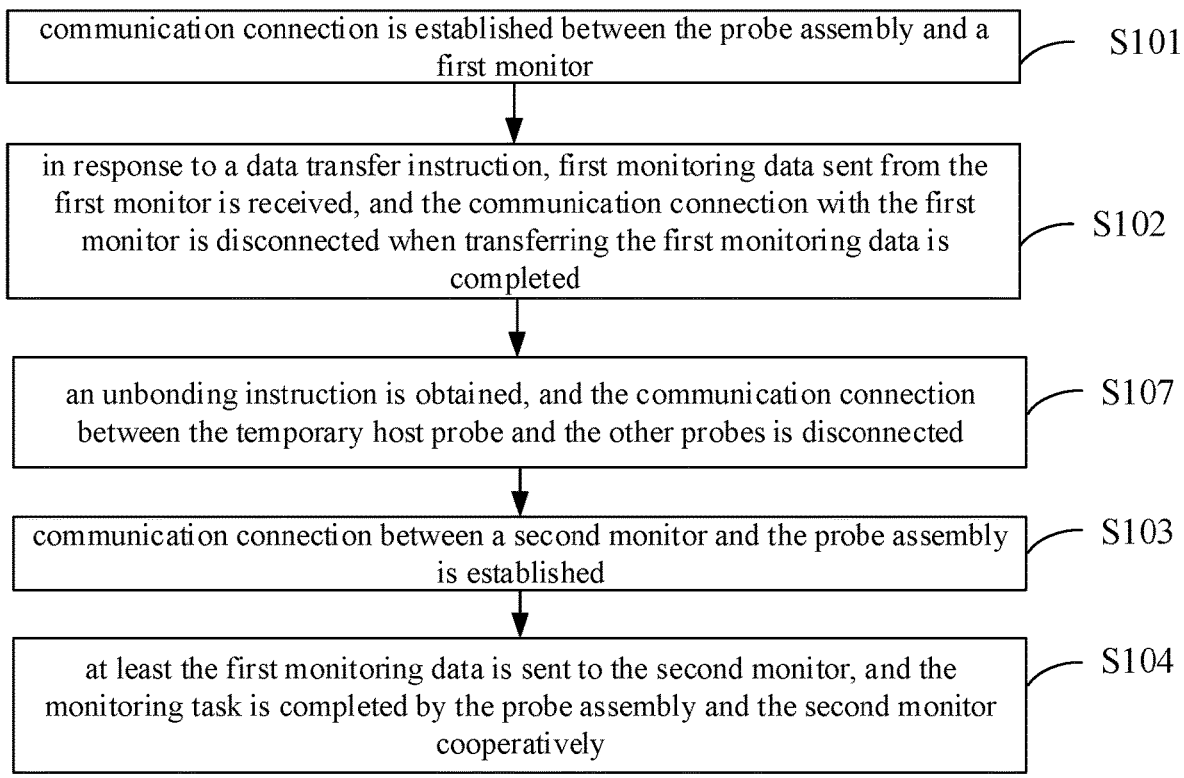
FIG. 4 is a flow chart of a method of managing monitoring data based on a probe assembly according to a third embodiment of the present disclosure.

As shown in FIG. 4, in some embodiments, before the operation S103, the method further includes the following.

In an operation S107, an unbonding instruction is obtained, and the communication connection between the temporary host probe and the other probes is disconnected.

Specifically, the temporary host probe sends the unbonding instruction to the other probes, and the communication connection between the temporary host probe and the other probes is disconnected. The unbonding instruction may include second access information corresponding to the second monitor. For example, the second access information may be an SSID and an access password of the second monitor.

Figure 5:
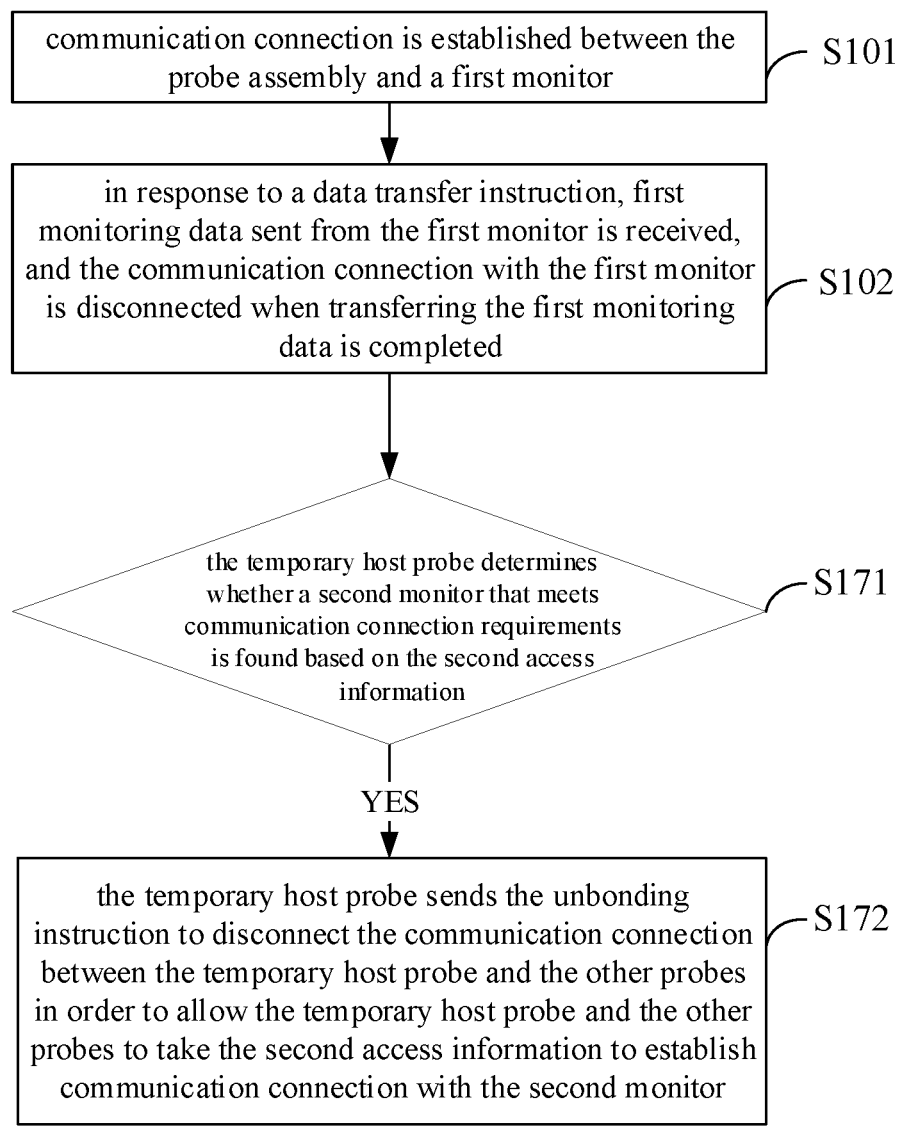
FIG. 5 is a flow chart of a method of managing monitoring data based on a probe assembly according to a fourth embodiment of the present disclosure.

As shown in FIG. 5, in an embodiment, the data-transfer instruction further includes: the second access information corresponding to the second monitor. For example, the second access information may be the SSID and the access password of the second monitor.

The operation S107 may include the following:

In an operation S171, the temporary host probe determines whether a second monitor that meets communication connection requirements is found based on the second access information.

In response to the second monitor that meets communication connection requirements being found, an S172 is performed.

In an operation S172, the temporary host probe sends the unbonding instruction to disconnect the communication connection between the temporary host probe and the other probes in order to allow the temporary host probe and the other probes to take the second access information to establish communication connection with the second monitor.

Specifically, the first monitor may obtain the second access information corresponding to the second monitor (such as the SSID and the access password of the second monitor) before a healthcare staff clicks the "transfer-out" button on the first monitor, i.e., before the first monitor sends the data-transfer instruction to the probe assembly. The first monitor programs, based on predefined coding rules, the access information of the temporary host probe and the second access information corresponding to the second monitor into the data-transfer instruction. The temporary host probe and the other probes receive the data-transfer instruction and parse the unbonding instruction to obtain the second access information corresponding to the second monitor. The temporary host probe actively searches for the second monitor based on the second access information. When a communication network of the second monitor is found, and when a signal strength of the found communication network meets connection conditions, the temporary host probe actively disconnects communication connection from the other probes connected to the temporary host probe and establishes communication connection with the second monitor. At this time point, the temporary host probe and the other probes are no longer connected to each other, and the temporary monitoring system is decomposed. The other probes establish the communication connection with the second monitor based on the second access information of the second monitor. In this way, a monitoring system that the second monitor communicatively connects with the temporary host probe and the other probes respectively is re-constructed.

According to the above method, the process of transferring from one bed to another is performed once on the first monitor only, where a serial number of the second monitor device is input. The process may be performed simply. However, the serial number of a monitor in a waiting room needs to be known in advance, and after the serial number is input, the data may be transferred to only the designated second monitor.

Figure 6:
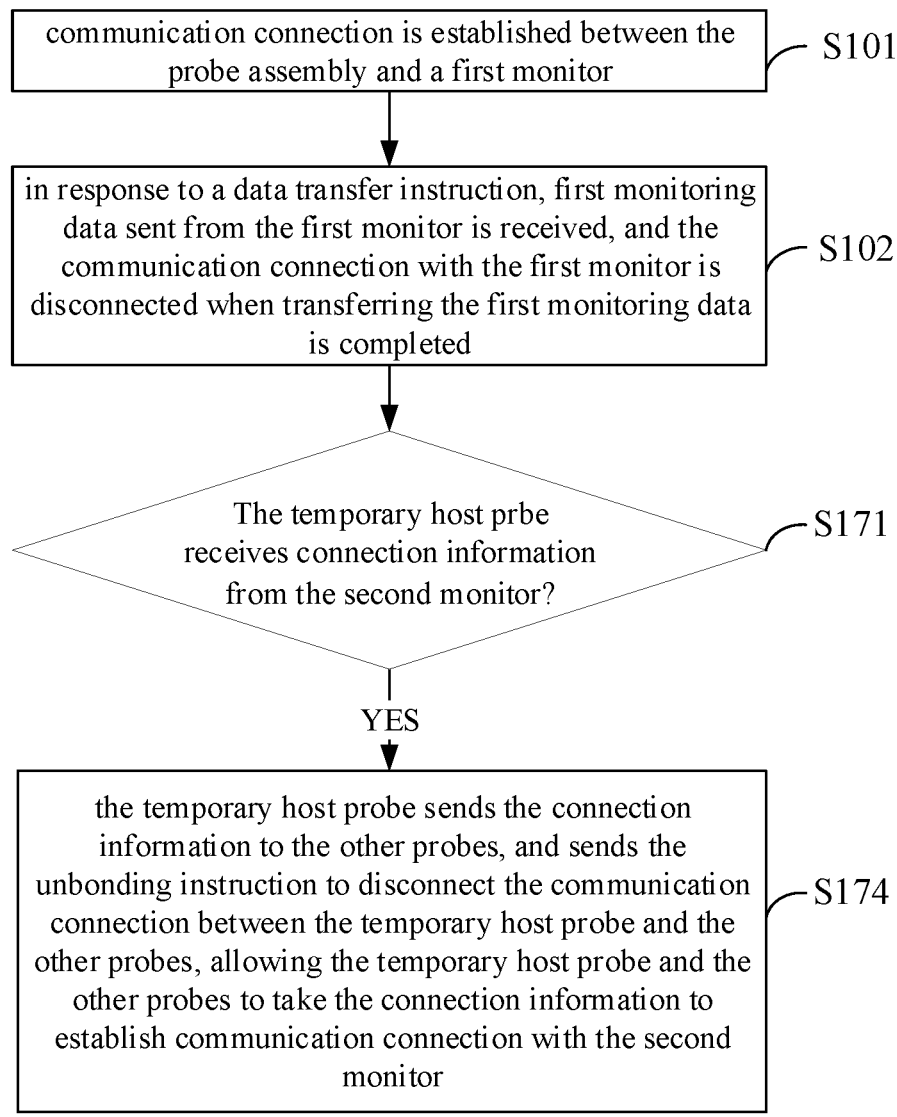
FIG. 6 is a flow chart of a method of managing monitoring data based on a probe assembly according to a fifth embodiment of the present disclosure.

As shown in FIG. 6, in some embodiments, the operation S107 includes the following.

In an operation S173, the temporary host probe determines whether the temporary host probe receives connection information from the second monitor.

In response to the temporary host probe receiving connection information from the second monitor, an operation S174 is performed.

In the operation S174, the temporary host probe sends the connection information to the other probes, and sends the unbonding instruction to disconnect the communication connection between the temporary host probe and the other probes, allowing the temporary host probe and the other probes to take the connection information to establish communication connection with the second monitor.

The second monitor may actively establish the communication connection with the temporary host probe. When the pregnant lady has been transferred to the delivery room, the second monitor obtains data-transfer instruction through the human-machine interface. The second monitor parses the data-transfer instruction to obtain the first access information. The second monitor actively searches a communication network of the temporary host probe based on the first access information. When the communication network of the temporary host probe is found, and when a signal strength of the communication network meets connection conditions, the second monitor actively establishes the communication connection with the temporary host probe and sends the second access information of the second monitor to the temporary host probe. The temporary host probe sends the second access information received from the second monitor to each of the other probes. After the other probes receive the second access information from the second monitor, the other probes actively disconnect from the temporary host probe and establish communication connection with the second monitor based on the second access information from the second monitor. At this time point, the temporary host probe and each of the other probes are no longer connected to each other, and the temporary monitoring system is decomposed. The temporary host probe establishes the communication connection with the second monitor based on the second access information of the second monitor. In this way, a monitoring system that the second monitor communicatively connects with the temporary host probe and the other probes respectively is re-constructed.

The above method is more flexible. Each monitor may serve as the second monitor to receive a connector and to allow the data to be transferred to. However, in this case, in the process of transferring from one bed to another, the data-transfer instruction needs to be entered on the second monitor.

Specifically, the second monitor may search and find the temporary host probe based on the first access information. The second monitor establishes the communication connection with the temporary host probe in response to the signal strength of the temporary host probe meeting a predetermined connection condition. The second monitor sends the second access information of the second monitor to the temporary host probe. The temporary host probe sends the unbonding instruction to at least one of the other probes and disconnects the communication connection with the at least one of the other probes. The unbonding instruction includes at least the second access information. The communication connection between the at least one of the other probes and the second monitor is established by taking the second access information.

Specifically, when the second monitor sends a sending instruction of the transfer-in instruction, the SSID and the password of the temporary host probe need to be known. When the pregnant lady has been transferred to the delivery room, the medical staff inputs the serial number of the first monitor (i.e., the transfer-out monitor, the monitor that the monitoring data is original connected to the probe assembly) in the second monitor (i.e., the transfer-in monitor, the another monitor that is going to be connected to the probe assembly), the second monitor converts the serial number of the first monitor into the first access information (i.e., the SSID and the password of the temporary host probe) based on preset rules (it may be agreed that SSIDs and passwords of all monitors are composed by another fixed content and the serial number of the device). The second monitor actively searches the temporary host probe based on the first access information. When the temporary host probe is searched and found, and when the signal strength of the temporary host probe meets the connection conditions, the second monitor actively initiates a connecting request to the temporary host probe and sends the SSID and the password of the second monitor when the connection is successful. The temporary host probe receives the SSID and the password of the second monitor and forwards the SSID and the password to other probes. At the same time, after the temporary host probe receives the SSID and the password of the second monitor, the temporary host probe disconnects connection from the other probes. The temporary host probe and the other probes initiate the connecting request to the second monitor. The second monitor responds to the wireless connecting request initiated by the temporary host probe and the other probes, and a network system where the second monitor and the probe assembly are connected with each other is constructed.

Figure 7:
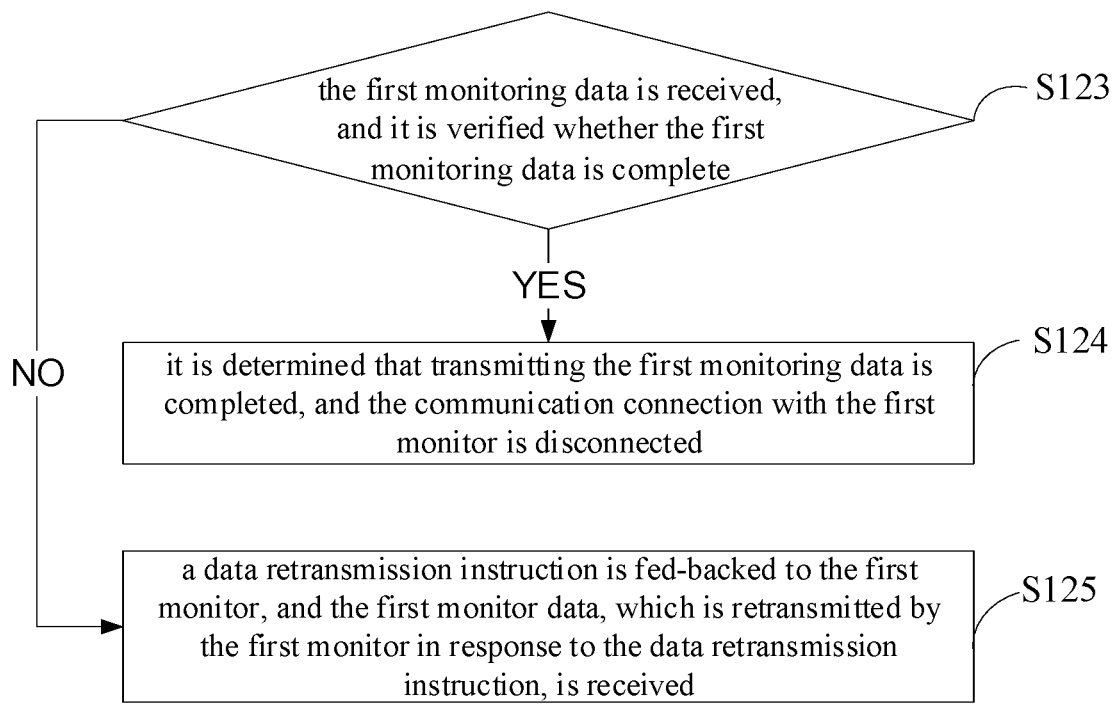
FIG. 7 is another flow chart of the operation S102 of the method shown in FIG. 1.

As shown in FIG. 7, in an embodiment, the operation S102 further includes the following:

In an operation S123, the first monitoring data is received, and it is verified whether the first monitoring data is complete.

Specifically, the temporary host probe verifies integrity of the first monitoring data by performing the following. The temporary host probe may obtain a return value of a data interface through an interface test tool. The temporary host probe may write the data interface to the interface test tool. The interface test tool may obtain the return value of the data interface. The return value of the data interface is data identified by a data identifier. For example, the interface test tool may be a postman tool. The temporary host probe performs data processing on the return value of the data interface by following data processing procedures of the data interface to obtain a verification value. In this way, the verification value is an expected return value of the data interface. The temporary host probe writes the data interface to the interface test tool, such that the interface test tool may obtain the return value of the data interface. In response to the return value of the data interface being the same as the verification value, the return value of the data interface is determined as matching the verification value, the data interface is normal, and the integrity of the first monitoring data is satisfied. In response to the return value of the data interface being not the same as the verification value, the return value of the data interface is determined as not matching the verification value, the data interface is abnormal, and the integrity of the first monitoring data is not satisfied.

In response to the integrity of the first monitoring data being satisfied, an operation S124 is performed. In the operation S124, it is determined that transmitting the first monitoring data is completed, and the communication connection with the first monitor is disconnected.

In response to the integrity of the first monitoring data being not satisfied, an operation S125 is performed. In the operation S125, a data retransmission instruction is fed-backed to the first monitor, and the first monitor data, which is retransmitted by the first monitor in response to the data retransmission instruction, is received.

Specifically, when the network is operating abnormally, the first monitoring data is incomplete, the temporary host probe of the probe assembly feeds the data retransmission instruction to the first monitor. The first monitor resends the first monitoring data in response to the data retransmission instruction, and the temporary host probe receives the retransmitted first monitoring data from the first monitor.

Figure 8:
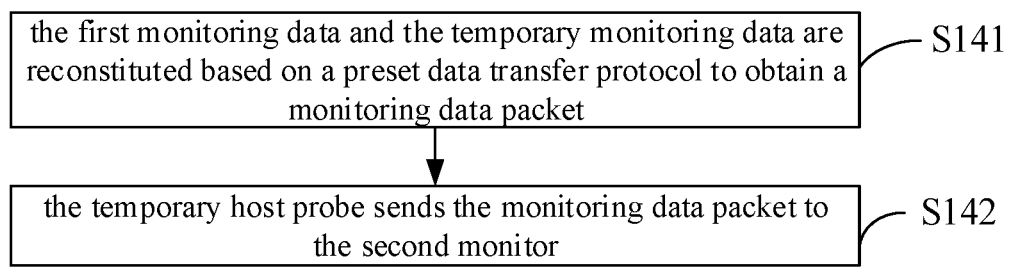
FIG. 8 is a first flow chart of an operation S104 of the method shown in FIG. 1.

As shown in FIG. 8, in an embodiment, the operation S104 includes the following.

In an operation S141, the first monitoring data and the temporary monitoring data are reconstituted based on a preset data transfer protocol to obtain a monitoring data packet.

In an operation S142, the temporary host probe sends the monitoring data packet to the second monitor.

Specifically, the reconstitution method based on the preset data transfer protocol is performed as follows. During the transfer-out period, the second monitoring data is after the first monitoring data. That is, the monitoring data collected by the fetal heart probe US1 during the process of transferring from one bed to another is spliced after the monitoring data collected by the fetal heart probe US1 of the first monitor. The monitoring data, such as the uterine contraction pressure and the automatic fetal movement, are spliced in a same way. In addition, relevant content of a file header is updated (such as an end time point of transferring from one bed to another, a duration of monitoring, and so on). At this time point, the temporary host probe of the temporary monitoring system sends the reconstituted monitoring data package to the second monitor, i.e., the temporary host probe sends the first monitoring data from the first monitor and the second monitoring data from at least one of the other probes during the transferring-out period to the second monitor.

Figure 9:
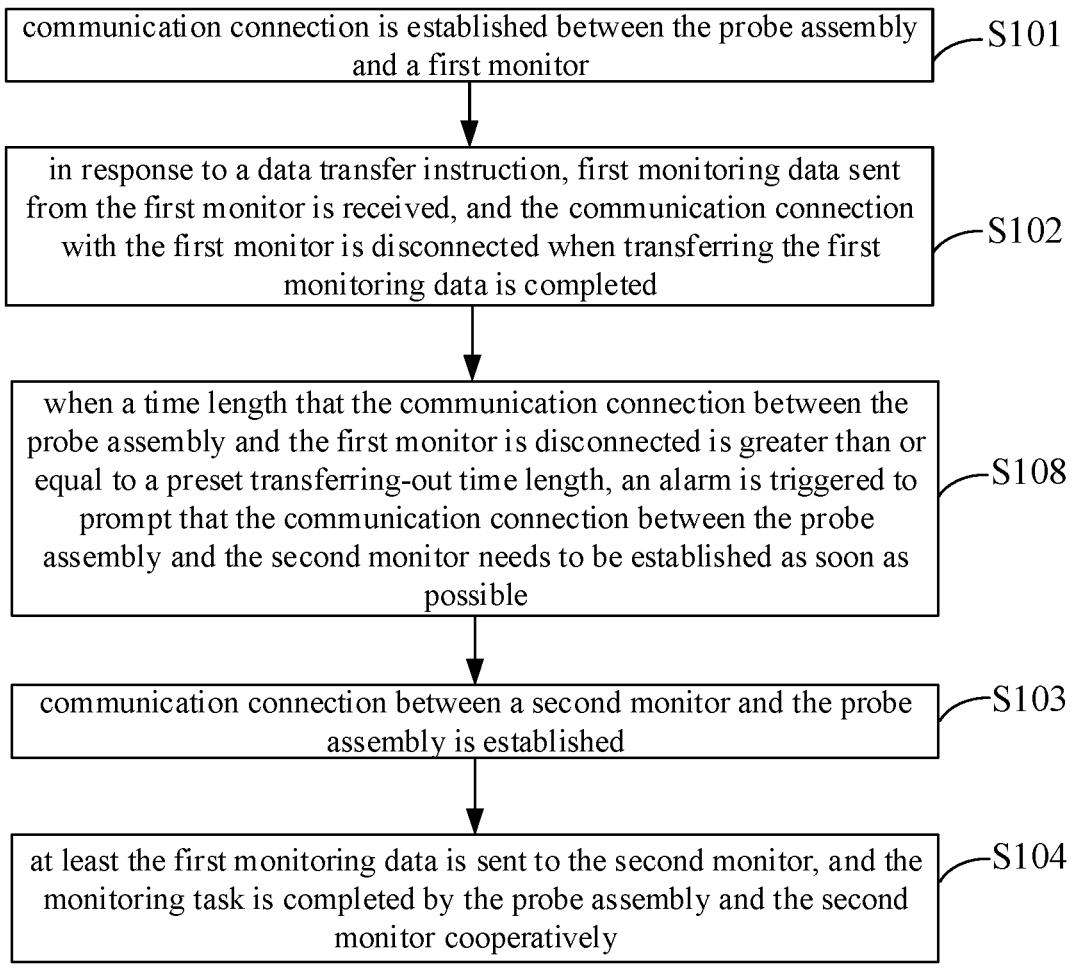
FIG. 9 is a flow chart of a method of managing monitoring data based on a probe assembly according to a sixth embodiment of the present disclosure.

As shown in FIG. 9, before the operation S103, the method further includes the following.

In an operation S108, when a time length that the communication connection between the probe assembly and the first monitor is disconnected is greater than or equal to a preset transferring-out time length, an alarm is triggered to prompt that the communication connection between the probe assembly and the second monitor needs to be established as soon as possible.

Specifically, in order to avoid not observing the monitoring data during the transferring-out period in a timely manner, which may result in missing important monitoring data, a preset transferring-out time length threshold may be set. When the transferring-out time length exceeds the preset transferring-out time length threshold (i.e., when the time length that the probe assembly is disconnected from the first monitor is greater than or equal to the preset transferring-out time length), the temporary host probe configured as the temporary host probe of the temporary monitoring system may trigger an alarm with an alarm tone and an alarm indicator to remind the healthcare staff to complete the transferring-out period as soon as possible. In addition, during the transferring-out period, a specific alarm may be triggered on the probe of the temporary monitoring system. For example, when the pregnant lady moves, causing the probe to deviate from an optimal position, causing no valid values to be measured, a relevant alarm may be triggered.

To be noted that, during transferring the patient from one bed to another, since the probe is not connected to any monitor, and an LCD of the probe can display limited content, exact content of the alarm may not be observed. Therefore, each probe emits a respective alarm. When the alarm is generated, the healthcare staff may troubleshoot the alarm based on their experiences. For example, when the US1 probe generates an alarm, the healthcare staff may only need to check a status of the US1 probe and observe whether the fetal heart rate is excessively low or excessively high, whether the US1 probe is positioned inappropriately, or whether the US1 probe is having a low power, and so on.

Figure 10:
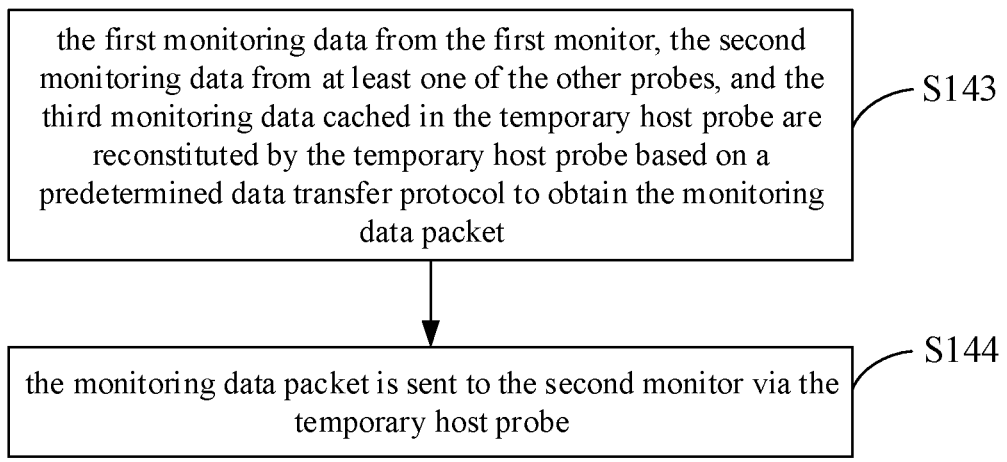
FIG. 10 is a second flow chart of an operation S104 of the method shown in FIG. 1.

As shown in FIG. 10, further, the operation S104 may include the following.

In an operation S143, the first monitoring data from the first monitor, the second monitoring data from at least one of the other probes, and the third monitoring data cached in the temporary host probe are reconstituted by the temporary host probe based on a predetermined data transfer protocol to obtain the monitoring data packet.

Specifically, the reconstitution method according to the preset data transfer protocol is as follows. The second monitoring data and the third monitoring data during the transferring-out period are spliced after the first monitoring data. That is, the monitoring data collected by the fetal heart probe US1 during the transferring-out period is spliced after the monitoring data collected by the fetal heart probe US1 from the first monitor, and the same splicing method is performed on the monitoring data such as the uterine contraction pressure, the automatic fetal movement, and so on. In addition, relevant content of the file header (such as the end time point of transferring the patient from one bed to another, time length of monitoring, and so on) is updated.

In an operation S144, the monitoring data packet is sent to the second monitor via the temporary host probe. At this time point, the temporary host probe of the temporary monitoring system sends the reconstituted monitoring data packet to the second monitor. That is, the first monitoring data from the first monitor, the second monitoring data from at least one of the other probes during the transferring-out period, and the third monitoring data from the temporary host probe during the transferring-out period are sent to the second monitor.

Figure 11:
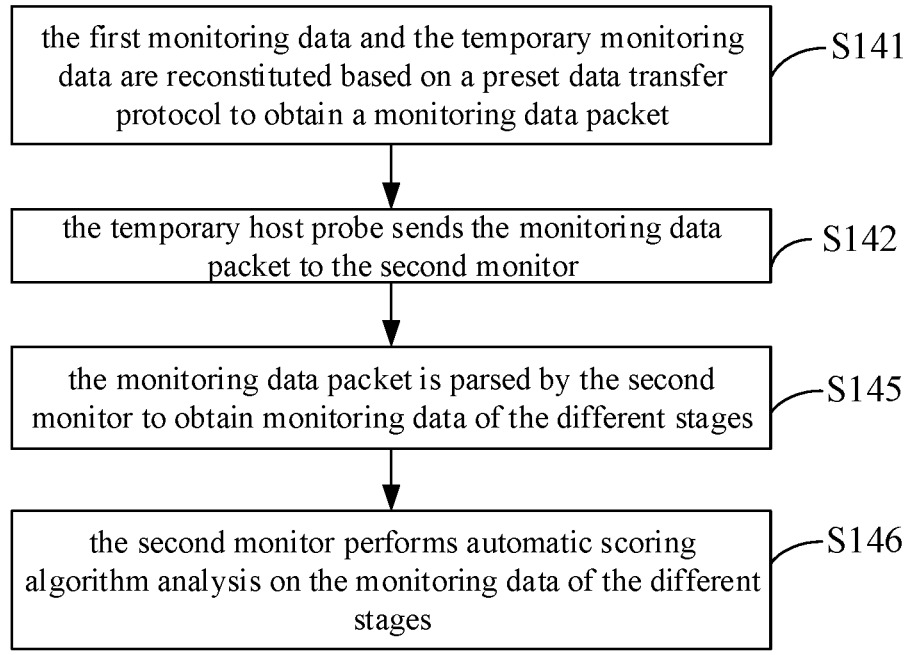
FIG. 11 is a third flow chart of an operation S104 of the method shown in FIG. 1.
Figure 12:
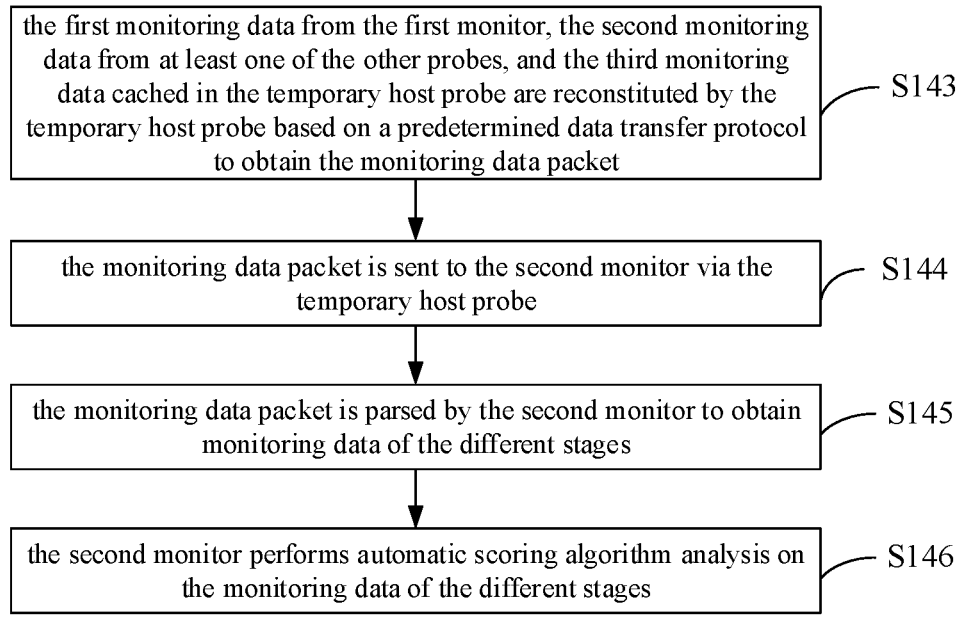
FIG. 12 is a fourth flow chart of an operation S104 of the method shown in FIG. 1.

As shown in FIGS. 11 and 12, after the operation S142 or the operation S144, the method further includes the following.

In an operation S145, the monitoring data packet is parsed by the second monitor to obtain monitoring data of the different stages.

Specifically, the second monitor receives the monitoring data packet and parses the monitoring data packet according to an agreed bad-transfer data transmission protocol to obtain the first monitoring data from the first monitor, the second monitoring data from at least one of the other probes during the transferring-out period, and the third monitoring data from the temporary host probe during the transferring-out period.

In an operation S146, the second monitor performs automatic scoring algorithm analysis on the monitoring data of the different stages.

Specifically, monitoring curves of the first monitoring data, the second monitoring data, and the third monitoring data may be plotted on a monitoring interface of the second monitor. Since each monitoring data records a starting time point and an end time point of transferring the patient from one bed to another, a time point of transferring out of one monitor and a time point of the transferring in another monitor may be marked on the monitoring interface, allowing the medical staff to view perform analysis easily. Clearly, data before the transferring-out marker is the first monitoring data from the first monitor, the data between the transferring-out marker and the transferring-in marker is the second monitoring data from at least one of the other probes and the third monitoring data from the temporary host probe, and the data after the transferring-in marker is the monitoring data that is collected by the probe assembly continually performing the monitoring tasks and operating cooperatively with the second monitor.

The monitoring curves may be plotted in different colours to distinguish the different stages of monitoring before, during and after transferring the patient from one bed to another. A time length of monitoring performed before the transferring-in may be determined after the transferring-in is completed successfully. When the time length of monitoring meets certain prenatal monitoring criteria, the relevant automatic scoring algorithm analysis may be activated to analyze the fetus in a timely manner.

Figure 13:
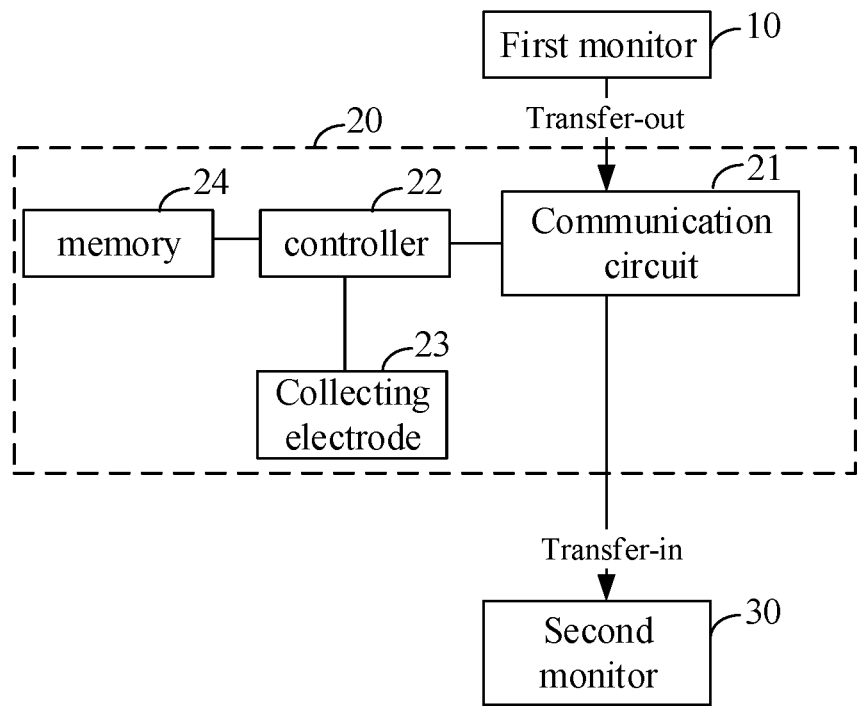
FIG. 13 is a structural schematic view of a probe assembly according to a first embodiment of the present disclosure.

As shown in FIG. 13, FIG. 13 is a structural schematic view of a probe assembly according to a first embodiment of the present disclosure. A probe assembly 20 includes a communication circuit 21, a controller 22, an acquisition electrode 23, and a memory 24. The controller 22 is electrically connected to each of the communication circuit 21, the acquisition electrode 23, and the memory 24.

The controller 22 is configured to control the communication circuit 21 to establish the communication connection with the first monitor 10 and to receive data-transfer instruction from the first monitor 10.

The controller 22 is further configured to control the acquisition electrode 23 and the memory 24 to perform the independent monitoring task in response to the data-transfer instruction.

The controller 22 is further configured to control the communication circuit 21 to receive the first monitoring data from the first monitor 10 and to disconnect the communication connection with the first monitor 10 when transmitting the first monitoring data is completed.

Specifically, the probe assembly 20 is arranged with the internal memory 24 to cache the first monitoring data from the first monitor 10. According to the TCP/IP protocol, the controller 22 may determine whether transmitting the first monitoring data is completed based on the return value of the data interface of the communication circuit 21.

When the communication circuit 21 is disconnected from the first monitor, the communication circuit 21 is not communicating with any monitor, and at this time point, the probe assembly 20 is in the transferring-out period. Since the pregnant lady is wearing the probe assembly 20 at all times, the monitoring task is not interrupted, and the probe assembly 20 is still collecting monitoring data within the transferring-out period.

The controller 22 is further configured to control the communication circuit 21 to establish the communication connection with the second monitor 30 and to send at least the first monitoring data to the second monitor 30.

The controller 22 is further configured to control the acquisition electrode 23 to operate cooperatively with the second monitor 30 to perform the monitoring task.

Specifically, when the communication circuit 21 successfully establishes the communication connection with the second monitor 20, the probe assembly 20 is in the transferring-in period, and the controller 22 controls the communication circuit 21 to send the first monitoring data from the first monitor 10, the second monitoring data and the third monitoring data collected by the collecting electrode 23 during the transferring-out period to the second monitor 30.

Figure 14:
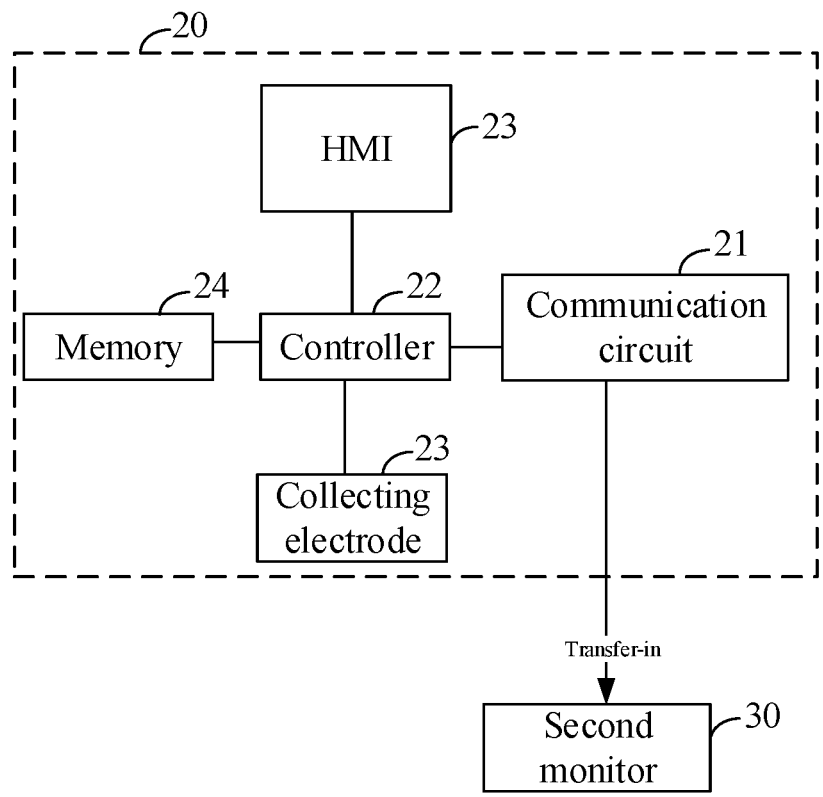
FIG. 14 is a structural schematic view of a probe assembly according to a second embodiment of the present disclosure.

As shown in FIG. 14, FIG. 14 is a structural schematic view of a probe assembly according to a second embodiment of the present disclosure. The probe assembly 20 further includes a human-machine interface 25, which is electrically coupled to the controller 22.

The probe assembly 20 is configured to obtain the second access information of the second monitor 30 through the human-machine interface 25 and to control, through the controller 22, the communication circuit 21 to establish the communication connection with the second monitor 30 based on the second access information of the second monitor 30.

Figure 15:
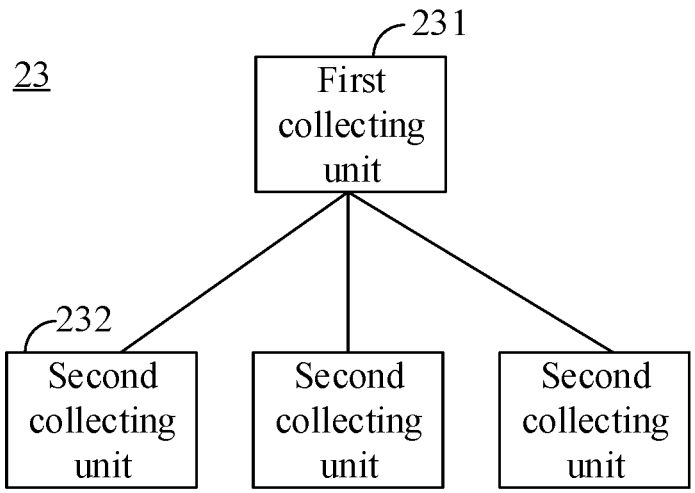
FIG. 15 is a structural schematic view of a probe assembly according to a third embodiment of the present disclosure.

As shown in FIG. 15, the acquisition electrode 23 includes a first acquisition unit 231 and at least one second acquisition unit 232. The controller 22 is further configured to control the at least one second acquisition unit 232 to perform the monitoring task on the user to obtain the second monitoring data. The memory 24 is configured to store the second monitoring data from the at least one second acquisition unit 232.

In an embodiment, the controller 22 is further configured to control the first acquisition unit 231 to perform the monitoring task on the user to obtain the third monitoring data. The memory 24 is configured to store the third monitoring data from the first acquisition unit 231.

Specifically, the probe assembly 20 is a temporary monitoring system. At this time point, the first acquisition unit 231 and the at least one second acquisition unit 232 are both in the transferring-out period and are no longer connected to any monitor. Since the first acquisition unit 231 and the at least one second acquisition unit 232 are worn by the pregnant lady during the transferring-out period, the monitoring task is not interrupted, and the probe assembly 20 is still collecting the relevant monitoring data and caching the relevant monitoring data in the internal memory 24.

Figure 16:
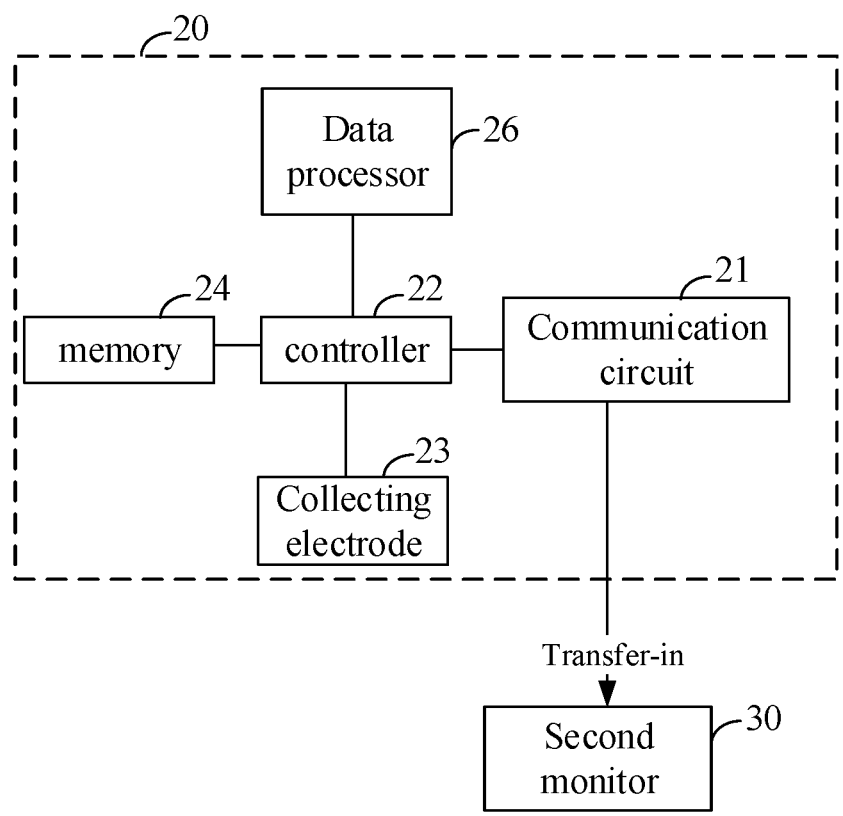
FIG. 16 is a structural schematic view of a probe assembly according to a fourth embodiment of the present disclosure.

As shown in FIG. 16, the probe assembly 20 further includes a data processor 26, electrically connected to the controller 22. The controller 22 is configured to control the data processor 26 to reconstitute the data from the first monitor data, the data from the second monitor, and the data from the third monitor based on the pre-determined data transfer protocol to obtain the monitoring data packet. The controller 26 is further configured to control the communication circuit 21 to send the monitoring data packet to the second monitor 30. The memory 24 is configured to store the monitoring data packet.

Specifically, the reconstitution method based on the pre-determined data transfer protocol is as follows. The second monitoring data and the third monitoring data during the transferring-out period are spliced after the first monitoring data. That is, the monitoring data collected by the fetal heart probe US1 during transferring the patient from one bed to another is spliced after the monitoring data collected by the fetal heart probe US1 from the first monitor, and the same splicing method is performed for the monitoring data such as the uterine contraction pressure, the automatic fetal movement, and so on. In addition, the relevant content of the file header (such as an end time point of transferring the patent from one bed to another, the time length of monitoring, and so on) are updated.

Further, the probe assembly 20 further includes a power supply, and the power supply is configured to provide power to the probe assembly 20.

Further, in an embodiment, the controller 22 is further configured to verify whether the first monitoring data is complete. When the first monitoring data is complete, the controller 22 controls the communication circuit 21 to disconnect the communication connection from the first monitor 10.

The present disclosure provides a probe assembly to perform the independent monitoring task in response to the data-transfer instruction during transferring the patient from one bed to another, and to store the monitoring data of the original monitor. After the probe assembly establishes the communication connection with the another monitor, the probe assembly may transfer the first monitoring data of the original monitor before the transferring to the another monitor. In this way, monitoring may be performed continuously, and the doctor may view the monitoring data before the transferring on the another monitor, the working efficiency of the doctor may be improved. In addition, the pregnant lady is wearing the probe assembly at all time while being transferred from one bed to another, the probe assembly may not be re-worn, and the process of transferring patient from one bed to another may be simplified.

The modules or units illustrated as separate components may or may not be physically separated. The components displayed as modules or units may or may not be physical modules or units, i.e., the components may be located at one place or may be distributed over a plurality of network modules or units. Some or all of these modules or units may be selected according to practical needs to achieve the purpose of the present disclosure.

In addition, various functional modules or units in various embodiments of the present disclosure may be integrated in one processing module or unit, or may be physically present separately, or two or more modules or units may be integrated in one module or unit. The above integrated modules or units can be implemented either in the form of hardware or in the form of software functional modules or units.

Technical solution of the present disclosure, or a part or all or part of the technical solutions which essentially contribute to the art, may be embodied in the form of a software product stored in a storage medium including a number of instructions to enable a computer device (which may be a personal computer, a server, or a network device, and so on) or a processor to perform all or part of the operations of each embodiment in the above. The aforementioned storage media include a USB flash drive, a portable hard drive, a read-only memory (ROM), a random access memory (RAM), a magnetic disk, or an optical disk, and other media that can store program codes.

Figure 17:
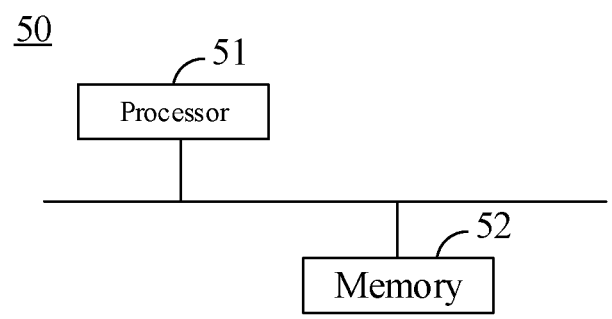
FIG. 17 is a structural schematic view of a probe assembly according to a fifth embodiment of the present disclosure.

As shown in FIG. 17, the probe assembly 50 includes: one or more processors 51 and a memory 52. The memory 52 is configured to store one or more programs, and the one or more programs are executed by the one or more processors 51.

To be noted that the processors 51 of the present embodiments execute the one or more programs to perform the operations in the method of managing the monitoring data based on the probe assembly described above. Details of the relevant content may be referred to the above method embodiments and will not be repeatedly described herein.

The memory 52 serves as a non-volatile computer-readable storage medium, configured to store non-volatile software programs, non-volatile computer executable programs, and modules. The processor 51 may run various non-volatile software programs, instructions, and modules in the memory 52 to perform various functional applications of the device and data processing.

Figure 18:
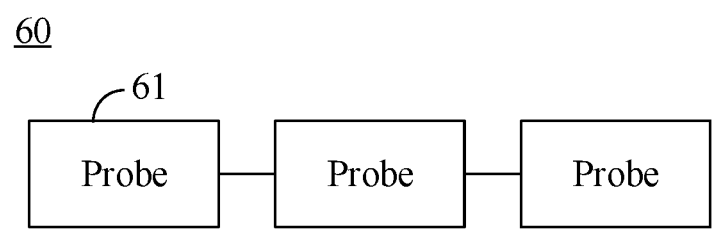
FIG. 18 is a structural schematic view of a probe assembly according to a sixth embodiment of the present disclosure.

As shown in FIG. 18, the probe assembly 60 includes a plurality of probes 61. To be noted that the plurality of probes 61 in the probe assembly 60 of the present embodiment operate cooperatively with each other to perform the operations in the above method of managing monitoring data based on the probe assembly. Details of the relevant content may be referred to the above method embodiments and will not be repeatedly described herein.

Figure 19:
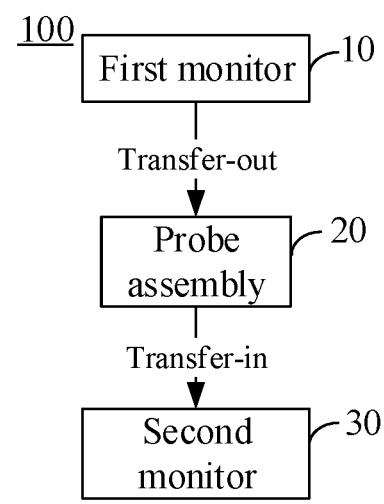
FIG. 19 is a structural schematic view of a management system of monitoring data according to an embodiment of the present disclosure.

As shown in FIG. 19, the monitoring data management system 100 includes: a first monitor 10, a probe assembly 20, and a second monitor 30. The probe assembly 20 operates cooperatively with the first monitor 10 and the second monitor 30 to perform the operations in the method of managing monitoring data based on the probe assembly described above. Details of the relevant content may be referred to the above method embodiments and will not be repeatedly described herein.

The probe assembly 20 is configured to establish the communication connection with the first monitor 10.

The probe assembly 20 is configured to receive the first monitoring data from the first monitor 10 in response to the data-transfer instruction and to disconnect the communication connection with the first monitor 10 when transmitting the first monitoring data is completed.

The probe assembly 20 is configured to establish the communication connection with the second monitor 30.

The probe assembly 20 is further configured to send at least the first monitoring data to the second monitor 30 and to perform the monitoring task cooperatively with the second monitor 30.

The probe assembly 20 is further configured to send the monitoring data packet to the second monitor 30.

The second monitor 30 is further configured to receive the monitoring data packet sent by the temporary host probe 301.

The second monitor 30 is further configured to parse the monitoring data packet to obtain monitoring data of the different stages, and to perform automatic scoring algorithm analysis on the monitoring data of the different stages.

The second monitor 30 is further configured to mark the first monitoring data, the second monitoring data, and the third monitoring data based on the monitoring time point.

The second monitor 30 is further configured to plot a monitoring curve based on the monitoring time point to distinguish between monitoring data obtained within a period when the probe assembly is performing the monitoring task cooperatively with the first monitor, monitoring data obtained within a period when the probe assembly is performing the monitoring task independently, and monitoring data obtained within a period when the probe assembly is performing the monitoring task cooperatively with the second monitor.

Specifically, monitoring curves for the first monitoring data, the second monitoring data, and the third monitoring data may be plotted on the monitoring interface of the second monitor. Since each monitoring data records the starting time point and the end time point of transferring the patient from one bed to another, the time point of transferring data out of one monitor and the time point of transferring the data in another monitor can be marked on the monitoring interface, allowing the medical staff to view and analyze the data easily. Clearly, the data before the transferring-out marker is the first monitoring data from the first monitor, the data between the transferring-out marker and the transferring-in marker is the second monitoring data and the third monitoring data from at least one of the other probes, and the data after the transferring-in marker is the monitoring data that is collected by the probe assembly continually performing the monitoring task cooperatively with the second monitor.

The monitoring curves may be plotted in different colours to distinguish between the different stages of monitoring before, during and after the transferring. The time length of monitoring performed before the transferring-in may also be determined after the transferring-in is performed successfully. When the time length of monitoring meets certain prenatal monitoring criteria, the relevant automatic scoring algorithm analysis may be activated to analyze the fetus in a timely manner.

The present disclosure provides a management system of monitoring data. In the process of transferring the patient from one bed to another, a temporary monitoring system is constructed by using the probe assembly in response to the data-transfer instruction. The monitoring data of the first monitor is stored in the temporary monitoring system. After the communication connection between the probe assembly and the second monitor is established, the probe assembly may transfer the first monitoring data of the first monitor before the transferring to the second monitor, such that monitoring may be performed continuously. The doctor may view the first monitoring data of the first monitor before the transferring on the second monitor, and the working efficiency of the doctor may be improved. In addition, the pregnant lady is wearing the probe assembly at all time while being transferred from one bed to another, the probe assembly may not be re-worn, and the process of transferring patient from one bed to another may be simplified.

The present disclosure further provides an apparatus having a storage function. The apparatus stores program data, the program data is capable of being executed by a processor to perform the operations in the above method of managing monitoring data based on the probe assembly. Details of the relevant content may be referred to the above method embodiments and will not be repeatedly described herein.

That is, the above-mentioned method of managing the monitoring data based on the probe assembly, when being implemented in software form and sold or used as a stand-alone product, can be stored in an apparatus that is readable by an electronic device and has the storage function. The storage apparatus having the storage function may include at least one of: a USB disk, a portable hard disk, a read-only memory, a random access memory, a magnetic disk, or an optical disk.

In the embodiments of the present disclosure, the disclosed method, probe assembly, system and apparatus for managing monitoring data based on the probe assembly can be implemented in other ways. For example, the various embodiments of the probe assembly described above are merely schematic. For example, division of functional modules or units is performed only based on logical functions. The functional modules or units can be divided in other ways when actually implemented. For example, multiple units or components can be combined or integrated into another system, or some features may be omitted, or not implemented. On another point, the shown or discussed mutual coupling or direct coupling or communicative connections may be indirect coupling or communicative connections via some interfaces, devices or modules or units, which may be electrical, mechanical or otherwise.

The foregoing shows only embodiments of the present disclosure, and shall not be interpreted as limiting the scope of the present disclosure. Any equivalent structure or equivalent process transformation using the specification and the accompanying drawings of the present disclosure, directly or indirectly applied in other related fields, is equally covered by the scope of the present disclosure.

What is claimed is:

1. A probe assembly, comprising a plurality of probes, wherein the plurality of probes in the probe assembly are configured to cooperate with each other to perform the operations of:
   establishing communication connection with a first monitor;
   receiving, in response to a data-transfer instruction, first monitoring data from the first monitor; after transferring the first monitoring data being completed, disconnecting the communication connection with the first monitor;
   establishing communication connection with a second monitor; and
   sending at least the first monitoring data to the second monitor and performing a monitoring task cooperatively with the second monitor;
   wherein the data-transfer instruction comprises: first access information; and
   while receiving, in response to the data-transfer instruction, first monitoring data from the first monitor; after transferring the first monitoring data being completed, disconnecting the communication connection with the first monitor, the plurality of probes are further configured to perform the operations of:
   selecting, based on the first access information, one probe from the plurality of probes to serve as a temporary host probe; and
   receiving the first monitoring data via the temporary host probe, and disconnecting the communication connection between the probe assembly and the first monitor after transmitting the first monitoring data is completed.

2. The probe assembly according to claim 1, wherein the selected probe comprises: a pre-defined probe or a probe which is in a first operating state; the probe which is in the first state has a power level and/or a signal strength greater than a power and/or a signal strength of any of the remaining probes of the plurality of probes; and the first access information comprises access information of the selected probe.

3. The probe assembly according to claim 2, wherein before establishing communication connection with the second monitor, the probe assembly are further configured to perform operations of:
   performing access configuration on the temporary host probe and the remaining probes by taking the first access information to establish temporary communication connection;
   collecting, continually by the temporary host probe and the remaining probes, monitoring data; storing, by the temporary host probe, the monitoring data that is continually collected by the temporary host probe; receiving and storing, by the temporary host probe, the monitoring data that is transmitted from the remaining probes; and generating temporary monitoring data based on the monitoring data collected by the temporary host probe and the monitoring data collected by the remaining probes.

4. The probe assembly according to claim 3, wherein before establishing communication connection with the second monitor, the probe assembly are further configured to perform operations of:
   obtaining an unbonding instruction and disconnecting the communication connection between the temporary host probe and the remaining probes.

5. The probe assembly according to claim 4, wherein the data-transfer instruction further comprises: second access information corresponding to the second monitor; and
   while obtaining the unbonding instruction and disconnecting the communication connection between the temporary host probe and the remaining probes, the probe assembly is configured to perform operations of:
   determining, by the temporary host probe based on the second access information, whether a second monitor satisfying communication connection requirements is searched and found; and
   sending, by the temporary host probe, the unbonding instruction in response to the second monitor satisfying communication connection requirements being found, and disconnecting the communication connection between the temporary host probe and the remaining probes, enabling the temporary host probe and the remaining probes to be ready to take the second access information to establish communication connection with the second monitor.

6. The probe assembly according to claim 4, wherein while obtaining the unbonding instruction and disconnecting the communication connection between the temporary host probe and the remaining probes, the probe assembly is configured to perform operations of:
   determining, by the temporary host probe, whether connection information from the second monitor is received; and
   sending, by the temporary host probe, the connection information to the remaining probes in response to the connection information from the second monitor being received, sending, by the temporary host probe, the unbonding instruction, disconnecting the communication connection between the temporary host probe and the remaining probes, enabling the temporary host probe and the remaining probes to be ready to take the connection information to establish communication connection with the second monitor.

7. A management system of monitoring data, comprising: a probe assembly, a first monitor, and a second monitor, wherein the probe assembly is configured to operate cooperatively with the first monitor and the second monitor to perform the operations of:
   establishing communication connection between the probe assembly and the first monitor;
   receiving, by the probe assembly in response to a data-transfer instruction, first monitoring data from the first monitor; after transferring the first monitoring data being completed, disconnecting the communication connection with the first monitor;
   establishing communication connection between the probe assembly and the second monitor; and
   sending, by the probe assembly, at least the first monitoring data to the second monitor and performing, by the probe assembly, a monitoring task cooperatively with the second monitor;
   wherein, the probe assembly comprises at least one probe;
   during receiving the first monitoring data from the first monitor, one probe of the at least one probe is selected to serve as a temporary host probe to receive and store the first monitoring data; and
   the communication connection between the probe assembly and the first monitor is disconnected after transmitting the first monitoring data is completed.

8. The management system according to claim 7, wherein the data-transfer instruction comprises: first access information, and the at least one probe comprises more than one probes; and during receiving the first monitoring data from the first monitor, one of the more than one probes is selected to serve as the temporary host probe.

9. The management system according to claim 8, wherein the selected probe comprises: a pre-defined probe or a probe which is in a first operating state; the probe which is in the first state has a power level and/or a signal strength greater than a power and/or a signal strength of any of the remaining probes of the more than one probes; and the first access information comprises access information of the selected probe.

10. A method of managing monitoring data based on a probe assembly, comprising:

establishing, by the probe assembly, communication connection with a first monitor;

receiving, by the probe assembly in response to a data-transfer instruction, first monitoring data from the first monitor; after transferring the first monitoring data being completed, disconnecting the communication connection with the first monitor; wherein, the first monitoring data comprises: monitoring data collected by the probe assembly from a patient, emergency treatment information recorded by the first monitor, and information of the patient;

establishing, by the probe assembly, communication connection with a second monitor; and sending, by the probe assembly, at least the first monitoring data to the second monitor and performing, by the probe assembly, a monitoring task cooperatively with the second monitor.

11. The method according to claim 10, wherein the data-transfer instruction comprises: first access information, and the probe assembly comprises more than one probes; and the receiving, in response to a data-transfer instruction, first monitoring data from the first monitor; after transferring the first monitoring data being completed, disconnecting the communication connection with the first monitor, comprises:

selecting, based on the first access information, one probe from the probe assembly to serve as a temporary host probe; and receiving the first monitoring data via the temporary host probe, and disconnecting the communication connection between the probe assembly and the first monitor after transmitting the first monitoring data is completed.

12. The method according to claim 11, wherein the selected probe comprises: a pre-defined probe or a probe which is in a first operating state; the probe which is in the first state has a power level and/or a signal strength greater than a power and/or a signal strength of any of the remaining probes of the more than one probes; and the first access information comprises access information of the selected probe.

13. The method according to claim 10, wherein the receiving, in response to a data-transfer instruction, first monitoring data from the first monitor; after transferring the first monitoring data being completed, disconnecting the communication connection with the first monitor, comprises:

receiving, by the probe assembly, the first monitoring data and verifying whether the first monitoring data is complete;

in response to the first monitoring data being complete, determining that transmitting the first monitoring data is completed and disconnecting communication connection between the probe assembly and the first monitor; and in response to the first monitoring data being incomplete, sending, by the probe assembly, a data retransmission instruction to the first monitor and receiving, by the probe assembly, the first monitoring data, which is retransmitted by the first monitor in response to the data retransmission instruction.

14. The method according to claim 12, wherein before the establishing communication connection with a second monitor, the method further comprises:

performing access configuration on the temporary host probe and the remaining probes by taking the first access information to establish temporary communication connection;

collecting, continually by the temporary host probe and the remaining probes, monitoring data; storing, by the temporary host probe, the monitoring data that is continually collected by the temporary host probe; receiving and storing, by the temporary host probe, the monitoring data that is transmitted from the remaining probes; and generating temporary monitoring data based on the monitoring data collected by the temporary host probe and the monitoring data collected by the remaining probes.

15. The method according to claim 14, wherein the sending at least the first monitoring data to the second monitor and performing a monitoring task cooperatively with the second monitor, comprises:

reconstituting the first monitor data and the temporary monitor data based on a predetermined data transmission protocol to obtain a monitoring data packet; and sending, by the temporary host probe, the monitoring data packet to the second monitor.

16. The method according to claim 14, wherein before the establishing communication connection with a second monitor, the method further comprises:

triggering an alarm to prompt establishing communication connection between the probe assembly and the second monitor as soon as possible, in response to a time length that the probe assembly is disconnected from the first monitor being greater than or equal to a preset transferring-out time length.

17. The method according to claim 14, wherein before the establishing communication connection with a second monitor, the method further comprises:

obtaining an unbonding instruction and disconnecting the communication connection between the temporary host probe and the remaining probes.

18. The method according to claim 17, wherein the data-transfer instruction further comprises: second access information corresponding to the second monitor; and the obtaining an unbonding instruction and disconnecting the communication connection between the temporary host probe and the remaining probes, comprises:

determining, by the temporary host probe based on the second access information, whether a second monitor satisfying communication connection requirements is searched and found; and sending, by the temporary host probe, the unbonding instruction in response to the second monitor satisfying communication connection requirements being found, and disconnecting the communication connection between the temporary host probe and the remaining probes, enabling the temporary host probe and the remaining probes to be ready to take the second access information to establish communication connection with the second monitor.

19. The method according to claim 17, wherein the obtaining an unbonding instruction and disconnecting the communication connection between the temporary host probe and the remaining probes, comprises:

determining, by the temporary host probe, whether connection information from the second monitor is received; and sending, by the temporary host probe, the connection information to the remaining probes in response to the connection information from the second monitor being received, sending, by the temporary host probe, the unbonding instruction, disconnecting the communication connection between the temporary host probe and the remaining probes, enabling the temporary host probe and the remaining probes to be ready to take the connection information to establish communication connection with the second monitor.

* * * * *